(12) United States Patent
Hainfeld

(10) Patent No.: US 7,183,072 B1
(45) Date of Patent: Feb. 27, 2007

(54) KIT FOR DETECTING HER-2/NEU GENE BY SITE-SPECIFIC METAL DEPOSITION

(75) Inventor: James F. Hainfeld, Shoreham, NY (US)

(73) Assignee: Nanoprobes, Inc., Yaphank, NY (US)

( * ) Notice: Subject to any disclaimer, the term of this patent is extended or adjusted under 35 U.S.C. 154(b) by 314 days.

(21) Appl. No.: 10/658,609

(22) Filed: Sep. 8, 2003

Related U.S. Application Data

(63) Continuation-in-part of application No. 09/822,131, filed on Mar. 30, 2001, now Pat. No. 6,670,113.

(51) Int. Cl.
*C12Q 1/26* (2006.01)

(52) U.S. Cl. ......................................... 435/25; 435/975

(58) Field of Classification Search ................... 435/25, 435/975
See application file for complete search history.

(56) References Cited

U.S. PATENT DOCUMENTS

| | | | |
|---|---|---|---|
| 5,116,734 A | 5/1992 | Higgs et al. ................... 435/28 |
| 6,358,682 B1 * | 3/2002 | Jaffee et al. .................... 435/6 |
| 6,911,306 B1 * | 6/2005 | Vertino ........................... 435/6 |
| 2005/0074457 A1 * | 4/2005 | Kamal et al. ............ 424/155.1 |

OTHER PUBLICATIONS

Press M. et al. Evaluation of Her-2/neu Gene Amplification and Overexpression. J of Clinical Onoclogy 20(14)3095-3105, Jul. 15, 2002.*

* cited by examiner

*Primary Examiner*—Ralph Gitomer
(74) *Attorney, Agent, or Firm*—Wilson Sonsini Goodrich & Rosati

(57) ABSTRACT

Disclosed are methods and materials for utilizing enzymes to act on metal ions in solution so that the ions are reduced to metal. Additionally disclosed is how to use enzymes to accumulate metal particles. The alteration of metal particles by enzymes interacting with the organic shell of the particles is also described. These methods enable a wide range of applications including sensitive detection of genes and proteins, use as probes for microscopy, nanofabrication, biosensors, and remediation.

6 Claims, 3 Drawing Sheets

US 7,183,072 B1

KIT FOR DETECTING HER-2/NEU GENE BY SITE-SPECIFIC METAL DEPOSITION

CROSS REFERENCE TO RELATED APPLICATIONS

This application is a continuation-in-part of U.S. patent application Ser. No. 09/822,131, filed Mar. 30, 2001, now U.S. Pat. No. 6,670,113, issued Dec. 30, 2003, the contents of which are incorporated by reference in their entirety.

FIELD OF THE INVENTION

The present invention relates to novel processes that permit biological enzymes to act directly on metals and metal particles. More particularly, one aspect of the invention relates to use of enzymes to selectively deposit metal. Other aspects of the invention relate to linking of metals to enzyme substrates, control of enzymatic metal deposition and applications of enzymatic metal deposition.

BACKGROUND OF THE INVENTION

Enzymes: Their Function and Uses

Enzymes are proteins, usually derived from living organisms, that are also catalysts for various metabolic or chemical reactions. Enzymes are therefore essential to all life. Recently, enzymes have been isolated, studied, altered, combined with other agents, and used in various processes. Uses of purified enzymes range from laundry detergents (where enzymes break down stains) to pathological detection of cancer (where enzymes produce a visible color product on tumor cells in a biopsy). Enzymes can be immobilized, for example by attaching the enzyme to a surface such as a bead, flat surface, or electrode using adsorption or covalent linkage. Immobilization allows the enzymes to be held in place for handling or to sustain washing without being removed. Immobilized enzymes can be used as biosensors, for example to measure glucose levels for diabetics.

As previously stated, enzymes are catalysts. As used herein a "catalyst" is defined as a material that increases the rate of a chemical reaction but is not itself consumed. At the end of a reaction, the catalyst is present in its original form so that it may act on new substrates. As used herein "substrate" is defined as a chemical that an enzyme works on to produce a new chemical. A "substrate" is the input material or "reactant" in the reaction catalyzed by the enzyme. Catalysts function by binding the substrate chemical or chemicals, and either introduce bond strain or orient reactants, thus making a transition or reaction possible at lower temperature or energy. Since enzymes are catalysts, they lower the activation energy barrier between two chemical states. Enzymes can, for example, facilitate the conversion of one chemical compound into another, or facilitate a reaction between chemicals. Without enzymes, reactions would be slow or, for most practical purposes, would not occur. This lowering of the activation energy barrier is one reason enzymes are required for living organisms. Enzymes control most body processes, and even cancer involves improper levels of certain enzymes regulating cell growth and death.

Enzymes fall into various classes relating to the type of reaction they catalyze, for example: oxido-reductases (such as dehydrogenases, oxidases); hydrolases (such as esterases, lipases, phosphatases, nucleases, carbohydrases, proteases); transferases; phosphorylases; decarboxylases; hydrases; and isomerases. Although enzymes within living cells act on specific compounds, it has been found that many enzymes will also act on other related compounds. Enzymes have also been found to perform similar reactions on synthetic or man-made substrates.

One use of enzymes is to perform reactions that convert a substrate into a detectable product. For example, a non-fluorescent compound may be converted into a fluorescent compound by cleavage of a particular bond using an enzyme. Alternatively, a colorless compound may be converted into a colored one by using an enzyme. Other uses of enzymes are deposition of a colored or otherwise detectable organic substrate from solution onto a solid support. This may be done by using an enzyme to make a soluble starting compound insoluble. Alternatively, enzymes can make a starting compound reactive, such as by forming a free radical thereof. The free radical subsequently reacts with, and binds to, the surrounding material. A useful embodiment of this technology is the ELISA test (Enzyme Linked ImmunoSorbant Assay), where, for example, an antigen is adsorbed to a solid support, such as a plastic microtiter plate well. To determine if an antibody to the antigen is present in a patient's serum, the serum is incubated in the coated well. If the antibody is there, it will bind to the immobilized antigen. After washing, a solution containing an anti-human antibody linked to the enzyme alkaline phosphatase is applied. The anti-human antibody will attach to any bound primary antibodies present. After washing, a substrate is applied, and if the alkaline phosphatase is present it will convert the colorless BCIP (5-bromo-4-chloro-3-indolyl phosphate) into a soluble color, which can then be measured spectrophotometrically. The amount of colored product produced is correlated with the amount of antibody in the serum, providing a quantitative measurement.

A number of significant advantages are gained by using enzymes for detection. These advantages include: a) Amplification: since the enzyme is a catalyst, and does not get used up in the reaction, and it can be used over and over. As more substrate is added more detectable product is produced. Except for practical limitations, the amount of product produced could be limitless. b) Linearity: the detectable product produced from the reaction of enzyme and substrate follows enzyme kinetics for that enzyme, and these can be relatively linear within some range. Even if the particular enzyme kinetics is not linear, the reaction may be calibrated. c) Selectivity: enzymes are usually very selective for the type of reaction and stereochemistry involved. Thus unwanted interferences may be reduced. d) Low background: if the conversion of the substrate to a colored or otherwise altered compound is negligible without the enzyme, then the background can be very low.

Enzymes themselves may be modified, for example, by genetic engineering or chemical modification, to produce alterations in specificity or reactivity, or to impart other characteristics, such as reduced immunogenicity (if the enzyme is to be used in vivo), or improved stability (for better shelf life or environmental tolerance).

A further expansion of the enzyme field relates to the use of unconventional material as biological catalysts, either proteins that are not normally enzymes, or non-protein material; for example, catalytic antibodies have been described.

Enzyme Substrates for Use in Detection Systems

The types of enzyme substrates popularly used for sensitive detection are typically calorimetric, radioactive, fluorescent or chemiluminescent. Conventional calorimetric substrates produce a new color (or change in spectral absorption) upon enzyme action. This type of detection is advantageous in that the colors produced are easily detected by eye or with spectral equipment. The cost of equipment for detection is also generally less than with other methods; for example in pathology, the brown color produced by the enzyme horseradish peroxidase acting on 3,3'-diaminobenzidine (DAB), requires only a simple bright field light microscope for observation of biopsied sections. A disadvantage of these calorimetric substrates is that they are generally of lower sensitivity than other enzyme methods.

Conventional radioactive substrates can enzymatically release or fix radioactivity for measurement. Although sensitive, this type of detection is becoming less popular due to the risks of handling and disposing of radioactive material, and since other methods now rival or exceed its sensitivity. Radioactive labeling for histochemical uses and autoradiography, typically require months to expose films, due to low specific activity, which is another disadvantage.

Conventional fluorescent substrates are popular since they are reasonably sensitive, generally have low backgrounds, and several differently colored fluorophores can be used simultaneously. A number of drawbacks, however, come with use of fluorescent substrates. Fluorescence requires expensive fluorescence optics, light sources and filters; by comparison, standard bright field microscopes are significantly less expensive. Fluorescence fades upon observation, sample storage or even exposure to room lights, thus making permanent or quantitative data difficult to achieve. Autofluorescence (fluorescence coming from certain compounds found naturally in many living organisms) from cells and other molecules can interfere with the test result. Standard tissue stains (such as nuclear fast red, hematoxylin, and eosin) cannot be seen simultaneously with the very different optics and illumination required for fluorescence detection, thus making visualization of landmarks of a tissue difficult. The standard viewing of tissues is done with bright field optics using colored stains and a standard microscope. Unfortunately, fluorescence is viewed using different illumination and sharp bandpass filters, so that only the fluorescent label is visible, and the general view of the stained tissue is not simultaneously available.

Chemiluminescence is based upon use of substrates that have sufficiently high chemical bond energies so that when the bonds are broken by an enzyme, energy is released in the form of visible light. This method has gained popularity due to the low background and very high sensitivity obtainable using photomultipliers, avalanche diodes or other sensitive light detectors. Alternatively photographic film can be used as a detection means. Chemiluminescence has a number of disadvantages. Detection requires expensive equipment or necessitates film development. The sample is not a permanent record, since the emitted light must be collected over time. Sensitive detection often requires lengthy light integration times of hours or even a day. Standard stains (such as nuclear fast red, hematoxylin, and eosin) cannot be seen simultaneously, thus making visualization of landmarks of a tissue difficult, for example. Only the emitted light from points in the specimen can be seen.

Additionally, all of the conventional detection schemes have some practical limitations for sensitivity. One limiting factor is the background, or non-specific signal generated. The background noise can come from various sources. For example with fluorescence detection the background can come from autofluorescence, fluorescent molecules that adhere to non-specific sites, light reflection off structures and other sources. Another limitation on detection method sensitivity is the amount of signal produced. For example, if an enzyme is used that has a low turnover, and produces only relatively few products, these few products will be harder to detect, and sensitivity will be worse than if a more efficient enzyme producing more products was used.

As mentioned earlier, since an enzyme is a catalyst and is not used up during reaction it can be fed more substrate, ideally forming product indefinitely. This provides a form of amplification. Of course there are practical limitations to enzyme amplification, such as the enzyme losing activity, the long times necessary to accumulate product, side reactions or other sources of background limit detection. Further, at some point the product produced may interfere with enzyme activity, either by shifting the reaction equilibrium, depositing products so as to impede flow to the active site of the enzyme or otherwise inhibiting the enzyme.

Although a number of enzyme based assays have been developed, one that is gaining popularity for sensitive detection is CAtalyzed Reporter Deposition (CARD), also known as Tyramide Signal Amplification (TSA, a trademark of New England Nuclear Corp, subsidiary of Perkin Elmer). In one variation of this method (there are several variations) a biotinylated antibody or nucleic acid probe detects the presence of a target by binding thereto. Next a streptavidin-peroxidase conjugate is added. The streptavidin binds to the biotin. Streptavidin is a protein isolated from the bacterium *Streptomyces*. Biotin is an organic compound having the formula $C_{10}H_{16}N_2O_3S$. A substrate of biotinylated tyramide (tyramine is 4-(2-aminoethyl)phenol) is used which presumably becomes a free radical when interacting with the peroxidase enzyme. The phenolic radical then reacts quickly with the surrounding material, thus depositing or fixing biotin in the vicinity. This process is repeated by providing more substrate (biotinylated tyramide) and building up more localized biotin. Finally, the "amplified" biotin deposit is detected with streptavidin attached to a fluorescent molecule. Alternatively, the amplified biotin deposit can be detected with avidin-peroxidase complex, that is then fed 3,3'-diaminobenzidine to produce a brown color. It has been found that tyramide attached to fluorescent molecules also serve as substrates for the enzyme, thus simplifying the procedure by eliminating steps. Although this type of assay has been used quite successfully, it has several drawbacks, including: expense of reagents, insufficient amplification, background problems, localization at the ultrastructural level (using electron microscopy) can be diffuse, and the limitations using fluorophores or chromophores mentioned previously.

Enzyme Biosensors

As used herein a biosensor is a device that uses biological materials to monitor the presence of a selected material, or materials, in a medium. Enzymes can be used in biosensor applications. Redox (reduction-oxidation) enzymes are used to generate an electrical signal, since electrons are transferred in redox reactions. Various other enzymes have been used in biosensors, and are selective for the following analytes, including use of beta-glucosidase to detect amygdalin, asparaginase for asparagine, cholesterol oxidase for cholesterol, chymotrypsin for esters, glucose oxidase for glucose, catalase for hydrogen peroxide, lipase for lipids, penicillinase for penicillin G, trypsin for peptides, amylase for starch, invertase for sucrose, urease for urea, and uricase for uric acid. Generally, biosensors achieve signal transduction using one of three approaches: amperometric, potentiometric and optical.

Amperometric biosensors work by enzymatically generating a current between two electrodes. The simplest design is based on the Clark oxygen electrode. The Clark oxygen electrode has a platinum cathode and a silver/silver chloride anode. Oxygen is reduced at the platinum cathode to water, and silver is oxidized to silver chloride at the anode. The rate of electrochemical reaction for the electrode is therefore dependent on the oxygen content of the solution. In a glucose monitor, glucose is a substrate for the immobilized glucose enzyme oxidase, which oxidizes glucose (consuming oxygen) to produce gluconic acid and hydrogen peroxide. This change in oxygen content alters the electrode current.

A variation on the above method measures the hydrogen peroxide produced by the enzymatic oxidation of glucose by making platinum the anode, and biasing it to 0.7 volts such that the hydrogen peroxide is oxidized back to oxygen, producing 2 electrons. Although the glucose oxidase is selective for glucose, and does not react with the closely related sugar fructose, some other molecules frequently found in the blood, either products of normal metabolism (e.g. uric acid) or drugs/medicaments taken orally (e.g. paracetamol or Vitamin C), can also break down directly and electrochemically at the electrode, bypassing the enzyme and giving a spurious signal. Similarly, the enzyme/device interface in other types of known biosensors is often prone to similar non-specific signals. In another variation redox enzymes may be coupled to other enzymes that interact with a specific substrate of interest to produce a product, the product then driving the redox enzyme.

Potentiometric biosensors are usually based on ion-selective electrodes. Such devices measure the release or consumption of ions during a reaction; the simplest potentiometric biosensor is based on a pH-probe. Glucose oxidase, for example, catalyzes the oxidation of glucose to gluconate, producing $H^+$ ions and hydrogen peroxide. The $H^+$ ions are then sensed by the pH probe. Detection is usually in the $10^{-4}$ to $10^{-2}$ M region, and therefore the above method generally lacks the accuracy and precision required for many analytes.

Optical biosensors have two common designs. In a first design light absorption is measured. An example is light absorption through a dye having a changed color that is the result of an enzyme driven pH change. A second design is based on measuring luminescence. An example is use of the enzyme firefly luciferase that reacts with ATP (adenosine triphosphate) and oxygen to produce AMP (adenosine monophosphate), $PP_1$ (inorganic pyrophosphate), oxyluciferin, $CO_2$ and a photon of light. This reaction can be coupled to any enzyme that produces or consumes ATP.

Metals and Enzymes

Some enzymes contain essential metal ions that are bound and required for activity. The metal ions aid in constraining the substrate for the reaction, but are not themselves consumed or deposited, they are part of the catalyst. Examples of enzymes that contain or require metal ions as cofactors are: alcohol dehydrogenase, carbonic anhydrase, and carboxypeptidase, which all require zinc ions; some phosphohydrolases and phosphotransferases require magnesium ions, arginase requires manganese ions; cytochromes, peroxidase, catalase, and ferredoxin contain iron ions; tyrosinase and cytochrome oxidase contain copper ions, pyruvate phosphokinase requires potassium ions, and plasma membrane ATPase requires sodium ions. However, these metal ions do not serve as substrates, are not linked to substrates and do not deposit as metal.

A very few metal ions are known to interact with enzyme reaction products. For example, the enzyme horseradish peroxidase can produce a diaminobenzidine (DAB) polymer. Nickel or cobalt ions complex with the DAB polymer to give the polymer a darker color. Unfortunately, this use has not been widely employed since the background goes up substantially, and little improvement in signal-to-noise ratio is generally found. Similarly osmium tetroxide can be added to the DAB polymer after it is formed. The osmium tetroxide reacts with the DAB product and leads to incorporation of the heavy metal, making the DAB deposit more visible in the electron microscope.

SUMMARY OF THE INVENTION

An object of the invention is to utilize enzymes to accumulate and/or deposit metal particles.

Another object of the invention is to utilize enzymes to act upon suitable metal ion substrates resulting in metal deposition.

Yet another object of the invention is to utilize enzymes to act upon suitable metal ion substrates to produce detectable changes.

Still another object of the invention is to utilize enzymes to act upon suitable metal ion substrates to produce quantifiable changes.

A further object of the invention to utilize enzymatic reactions that act on ligands attached to metal particles to produce detectable changes.

A still further object of the invention to utilize enzymes to act on substrates liganded to metal surfaces to produce quantifiable changes.

One embodiment of the present invention describes a method for using enzymes to selectively catalyze metal deposition. As used herein "metal deposition" is defined as a buildup or accumulation of metal (metallic elements in the zero oxidation state) in the vicinity of the enzyme. Typically, metal deposition will start within a distance of about 1 micron from the enzyme. Naturally as metal deposition continues the metal accumulation may extend beyond this distance. Two aspects are disclosed. In a first aspect, metal nanoparticles having a diameter in the range of about 0.8 to 50 nm are linked to, or contain, compounds that are acceptable enzyme substrates. When the enzyme deposits the substrate compound, the metal particles are co-deposited. In a second aspect enzymes, or modified enzymes, are used to directly reduce metal ions to deposit metal. As used herein "modified enzymes" in this specific context are defined to be enzymes that are pretreated with a solution of metal ions before a reducing and oxidizing agent are added. Extensions of the above embodiments included as inventive aspects include electrochemical or electroless plating of the same or a different metal over the metal particle or deposit.

In other embodiments of the present invention various applications for using the enzymatically deposited metals are disclosed. For example, the inventive enzymatically deposited metals may be used for highly sensitive gene detection, sensitive immunodetection, novel biosensor designs, bacterial detection, remediation and nanofabrication of novel materials.

In yet another embodiment of the present invention, a test kit is provided for enzymatically depositing metal in a zero oxidation state. The test kit comprises means for enzymatically depositing metal in a zero oxidation state, and the enzymatically deposited metal provides a detectable test result.

The novel forms described for metals, and/or metal-ligand complexes, participating as substrates for enzymes lead to very distinct advantages over known methods of detection. Some of these advantages are listed below.

No harmful radioactivity need be handled or disposed of to achieve comparable or better sensitivity in assays. No lengthy time of exposure is needed (autoradiograms can take several months to expose). No film, film processing or film chemicals are required.

Gold nanoparticles have extinction coefficients about 1,000 times higher than highly colored compounds or fluorophores. Therefore, their use substantially increases sensitivity.

No expensive fluorescent optics, light sources or filters are required. There is no fading of the sample upon observation or storage or exposure to room lights. Autofluorescence from cells and other molecules does not create any interference. Standard stains (such as nuclear fast red, hematoxylin and eosin) can be used and seen simultaneously with the enzyme deposited metals, making visualization of landmarks of a tissue simple.

No expensive chemiluminescence equipment and/or film development is necessary. The enzyme deposited metals create a permanent record. Sensitive detection can be relatively quick. No expensive chemiluminescent substrates are needed.

The invention disclosed herein utilizes an enzyme reaction for deposition or product formation. The deposition rates are determined by enzyme kinetics, which result in linear or easily calibrated rates of reaction. This makes the invention much more suitable for quantitative detection than conventional autometallographic methods of depositing metal on nucleating particles. Additionally the invention does not suffer from irregular rates of deposition from particle to particle as is known to occur with conventional autometallographic methods.

The present invention has an inherent amplification step since an enzyme catalyst is used. Thus the invention can provide more sensitive detection than is possible with non-enzymatic methods, such as direct immunolabeling with a fluorophore or chromophore.

Compared with, for example, deposition of an organic molecule; enzymatic metal deposition makes possible many additional detection methods including by x-rays, electron microscopy, electrochemical, optical, magnetic, and many others. Many of the additional test methods useful with enzymatic metal deposits are exceedingly sensitive, and permit assays more sensitive and/or rapid than is possible with conventional test methods.

In general, the material of the invention may be alternately formulated to comprise, consist of, or consist essentially of, any appropriate components herein disclosed. The material of the invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DETAILED DESCRIPTION OF A PREFERRED EMBODIMENT

Figure 1:
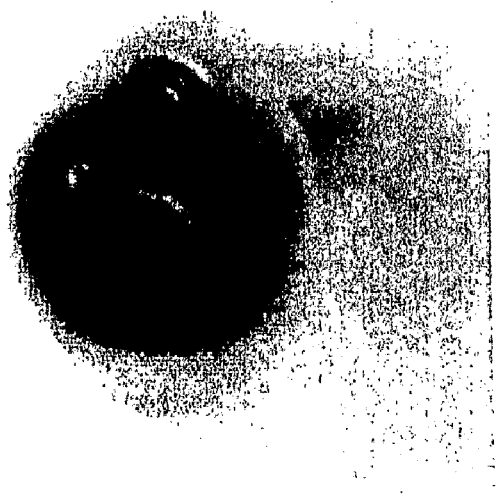
FIG. 1 illustrates the results of a conventional blot test showing color developed by peroxidase acting on DAB (3,3'-diaminobenzidine). One microliter containing one microgram of the enzyme horseradish peroxidase was applied to a piece of white nitrocellulose membrane and permitted to dry. Next, 1 ml of 50 mM TRIS buffer, pH 7.6 was applied containing 10 microliters of 10% DAB and 10 microliters of 3% hydrogen peroxide. Note that when a hydrogen peroxide concentration is used in this application, that concentration is the final or absolute concentration of hydrogen peroxide in the solution. In a few minutes, a brown color appeared over the area containing the peroxidase (the central spot). However, some background is apparent surrounding this spot, as evidenced by the brown color on the rest of the membrane. The blot was washed with water to stop the reaction. The blot is magnified 7 times.
Figure 2:
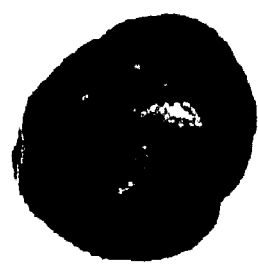
FIG. 2 illustrates the results of a blot test incorporating one aspect of the invention showing a signal developed by enzyme metal deposition. Similarly to the procedure used in FIG. 1, one microliter containing one microgram of the enzyme horseradish peroxidase was applied to a piece of white nitrocellulose membrane and permitted to dry. Next the blot was incubated with 1 ml of 0.2% silver acetate in water for 3 minutes. The blot was washed twice with water and a 1 ml solution (comprising 2.5 mg/ml hydroquinone, 1 mg/ml silver acetate, and 0.06% hydrogen peroxide in 0.1 M citrate buffer, pH 3.8) was applied. In under a minute, a black colored silver metal deposit appeared over the area containing the peroxidase. The blot was washed with water to stop the reaction. Compared to the conventional reaction shown in FIG. 1, the enzyme metal deposition of this invention shows a much denser and more visible product, and shows no background deposition outside the enzyme area. The blot is magnified 7 times.

One aspect of the invention relates to constructing substrates for enzymes that contain metal particles in the range of about 0.8 to 50 nm in diameter. It should be noted that the terms metal particles and metal clusters are interchangeably used to refer to metal particles. This concept has not been effected nor is it deemed possible by those skilled in the art for several reasons. Enzymes are highly specific; for example, glucose oxidase will accept glucose and not the closely related sugar fructose. Additionally enzymes are stereospecific. Coupling a "large" metal sphere (large in comparison to the substrate, for example the metal sphere is sometimes twice the substrate size) to the substrate may alter the substrate structure or present steric hindrances that would interfere with enzyme activity. The accepted approach is to enzymatically deposit a small molecule, such as biotin, then detect this with streptavidin which is pre-coupled to a gold particle.

Surprisingly, the inventor has discovered that some metal particle-enzyme substrates, are accepted by some enzymes, and result in specific deposition of metal particles. One mechanism of metal particle deposition is believed to include oxidation or reduction of the substrate forming a species that polymerizes and accumulates creating an insoluble mass. In another possible mechanism, bonds in the substrate are broken or made which release or alter solubilizing moieties; the substrate is converted from a soluble compound into an insoluble material, which then builds up around the enzyme. In a further possible mechanism the enzyme creates a free radical on the substrate, making it highly reactive; the free radical substrate attaches to solid material around the enzyme and is covalently fixed in place. Continued enzyme action adds more product, thus building up a deposit.

This discovery, which as explained above is contrary to both skilled opinions and current practices, has significant advantages. For example, directly depositing metal particles eliminates steps in the existing method of biotin deposition followed by streptavidin-gold (or other similar processes), thus reducing time and costs. It also brings the metal particles closer to the enzyme for better spatial resolution. Improved spatial resolution is important for electron microscopy localizations and nanofabrication. Since the metal is deposited directly, the efficiency and occupancy of deposition at enzymatic sites is improved. For electrochemical applications, tunneling and charge conduction is highly dependent on particle spacing, and the new method permits particles to be deposited so that useful conduction may be achieved. Hence, a number of significant benefits are achieved by this aspect of the invention.

As an example, gold particles in the range of about 0.8 to 50 nm may be synthesized by reduction of gold salts or gold compounds. For example, $HAuCl_4$ at 0.01% by weight in water is reduced by 2 milliMolar sodium citrate in boiling water to produce approximately 10 nm gold particles. By changing the amount of citrate, different sized gold particles may be produced. Other reducing agents (besides citrate) and recipes are known for producing metal particles in the size range of about 0.8 to 50 nm. An organic layer or shell may be bound to the metal particle surface, typically consisting of thiol compounds, phosphines, polymers, proteins or other compounds. The use of the term organic layer or shell is also meant to include partial or incomplete coverage of the metal particle surface. Some metal particles have these organic coatings attached by adsorption, whereas others are attached by covalent bonding between surface metal atoms and, for example, sulfur or phosphorus atoms.

Various methods were found to attach the enzyme substrate to the metal particle. In one method reactive groups (e.g., amines) of the metal particle organic layer are used to crosslink to the enzyme substrate. For example, a gold particle stabilized with phosphines containing at least one aminophoshine may be coupled via the aminophosphine to 3,3'-diaminobenzidine. The coupled gold particle-3,3'-diaminobenzidine then becomes a substrate for horseradish peroxidase, resulting in deposition of gold particle.

In another method the substrate is incorporated directly into the metal particle organic layer. Gold particles were formed from gold salts reduced with sodium borohydride in the presence of glutathione and 3,3'-diaminobenzidine (DAB), then purified by column chromatography to remove unreacted starting materials. The glutathione and DAB are incorporated into the gold particles. These gold particles were found to be deposited by horseradish peroxidase in the presence of hydrogen peroxide. Alternatively gold particles can be made from gold salts reduced with sodium borohydride in the presence of glutathione and 4-hydroxythiophenol, then purified by column chromatography to remove unreacted starting materials. The gold particles with incorporated substrate so produced were found to be deposited by horseradish peroxidase in the presence of hydrogen peroxide.

In a further method, gold particles stabilized by thioglucose were found to be deposited from solution by horseradish peroxidase if hydroquinone and hydrogen peroxide were included in the solution. These deposited gold particles contained glucose and were also demonstrated to have activity with the enzyme glucose oxidase.

Another aspect of the invention is the enzymatic alteration of the metal particle coating. This aspect of the invention is applicable even if the metal particles are already deposited and remain deposited, or become soluble, or if the particles are in solution and remain in solution after the enzymatic reaction. For example, a phosphatase will cleave a phosphate group linked to the surface of a gold cluster or particle, thus changing its net charge. The gold particles may remain in solution, but will now move differently in an applied electric field, and therefore the gold particles will electrophorese differently. Since the gold particles are highly visible and detectable, a sensitive assay of phosphatase activity may be achieved using this phenomenon.

Another example of a novel enzymatic alteration of a metal particle is the proteolytic cleavage of a protein or peptide bound to a metal particle. Upon action of, for example, proteinase K or trypsin, some of the protein shell attached to the metal particle was cut by the enzyme and released, resulting in alteration of the absorption spectrum or in some cases aggregation of the metal particles.

Another aspect of the invention is expansion from use with metal particles to metal surfaces generally. Most of the ligands that stabilize and bind to metal particles also adhere to metal surfaces. As used herein "ligand" is defined to be a material that is attached to a metal particle or metal surface. As previously discussed the same, or similar, ligands can be used to attach terminal phosphate groups to a metal surface (e.g., using derivatized thiolalkanes or phosphines). Alternatively, the metal particles may be immobilized on a surface. Upon exposure to alkaline phosphatase, the phosphate groups would be cleaved, thus changing the charge of the metal surface. This change can be sensed using an electrostatic balance or by testing conductivity of the solution. Thus, metal surfaces are useful platforms for many devices, where enzyme surface alterations can be sensed by optical changes (using reflectance, or other methods), mass changes (sensed by e.g., a quartz microbalance whose frequency shifts with mass), electrical changes (e.g., of conductivity), or other methods.

Metal ions are not believed to be substrates for enzymes. Although some enzymes require metals as part of their active site, the metals themselves are not used up, but instead form part of the catalytic site with the enzyme to effect other reactions. Most metal ions are cations and require reduction and electrons for conversion to metal (zero oxidation state). The inventor is not aware of a teaching that oxidoreductase, or any other, enzymes might be useful to catalyze such reactions. In fact upon further investigation of the properties of peroxidases such a reaction would seem unlikely. Horseradish peroxidase, contains as a cofactor ferriprotoporphyrin (a heme group). When bound to the enzyme, the iron is in the +3 state and linked to a hydroxyl group. This hydroxyl group can be displaced by other anions, including cyanide, azide, fluoride, and its substrate, hydrogen peroxide. The reaction sequence of horseradish peroxidase is proposed to be:

a) Enzyme-$H_2O$+$H_2O_2$→Enzyme-$H_2O_2$(complex I)+$H_2O$ b) Enzyme-$H_2O_2$+$AH_2$→complex II+AH.

c) complex II+AH.→Enzyme-$H_2O$+A where $AH_2$ is the reduced substrate and A is the oxidized substrate. Note that the substrate goes through a free radical form in step b wherein the free radical is denoted by the dot: "AH.". As an example, peroxidases catalyze the following reaction:

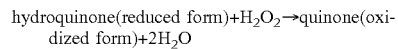
hydroquinone(reduced form)+$H_2O_2$→quinone(oxidized form)+$2H_2O$

Typically, an organic substrate is oxidized, while hydrogen peroxide is reduced. This is contrary to usage for metal ion reduction since it is desired to reduce the metal ion, not oxidize it. Furthermore, hydroquinone can reduce some metal ions (depending on concentrations and place in the electrochemical series, which orders half-reactions by redox potential). However peroxidase would remove hydroquinone from solution, instead generating the oxidized form (quinone), which will not reduce metal ions. One would logically conclude that peroxidases were therefore not suitable for reduction of metal ions.

Contrary to the above conclusion, a surprising and unexpected discovery was made that under some circumstances, enzymes can accept metal ions themselves as a substrate and reduce those metal ions to metal. Further the enzymes can deposit the reduced metal. For example, if horseradish peroxidase is combined with silver ions (silver acetate was used originally), and an appropriate reducing agent is added, e.g., hydroquinone, no enzyme-mediated reduction of metal occurs. However, upon addition of hydrogen peroxide, the enzyme accepts silver ions as a substrate and reduces them to silver metal, resulting in a metallic deposit (a citrate buffer was used at pH 3.8). Therefore another aspect of the invention is enzymatic reduction of metal ions.

It was found that bovine serum albumin and other non-enzyme proteins, for example, IgG, collagen, actin and myosin, when substituted for peroxidase, do not serve to deposit metal. This further confirms that the inventive metal deposition is enzymatic in nature.

Further exploration of this phenomenon revealed that pretreatment of the enzyme with gold ions (e.g., from potassium tetrabromoaurate), or silver ions (e.g., from silver acetate), followed by optional washing (to remove the excess pretreatment metal ion solution), resulted in greatly enhanced rates of silver deposition when the developing mix was subsequently applied. As used herein the term "developing mix" is defined as the solution applied to the enzyme to obtain metal deposition. Typically the developing mix contains metal ions (e.g., silver acetate), a reducing agent (e.g., hydroquinone) and an oxidizing agent (e.g., hydrogen peroxide) in a controlled pH buffer (e.g., 0.1M sodium citrate, pH 3.8). In the above enzymatic metal reduction the developing mix advantageously comprised silver acetate, hydroquinone, and hydrogen peroxide in a citrate buffer at a pH of about 3.8. One preferred developing mix consists of 2.5 mg/ml hydroquinone, 1 mg/ml silver acetate, and 0.06% hydrogen peroxide in 0.1 M citrate buffer, pH 3.8. The enzymatic metal reduction and deposition can be conveniently observed when the enzyme is immobilized, for example, either on nitrocellulose paper, or immunologically attached to a target antigen.

Although the exact mechanism of this aspect of the invention has not been completely elucidated, it may be that hydrogen peroxide is reduced by the enzyme, but some electrons become available to also reduce silver metal. The hydroquinone is oxidized. It appears that peroxidase or its cofactor may similarly bind the pretreatment metal ions. These bound pretreatment metal ions then either enhance or retard the enzymatic reduction of metal ions supplied in the developing mix. The binding of metal ions (e.g., gold or silver) before the developing mix is applied may explain the alteration in metal deposition rates seen when the developing mix is applied. Thus, another aspect of the present invention comprises alteration of enzyme specificity using a developing mix to allow the enzyme to accept metal ions. A further aspect of the invention is modulation of the rate of metal deposition by pretreatment of the enzyme.

As discussed above a wide range of silver or gold pretreatment concentrations, including about 0.2% silver acetate or about 0.01% potassium tetrabromoaurate, serve to greatly enhance metal deposition. Surprisingly, use of more dilute pretreatment concentrations, particularly including about 0.01% silver acetate is found to substantially inhibit the subsequent enzymatic deposition reaction. While inhibition of the enzymatic reaction was unexpected, it provides a method to retard the enzymatic deposition of metals. Thus, another aspect of the invention provides methods to both stimulate and retard the enzymatic deposition of metals, thereby allowing further control of the enzymatic metal deposition process.

Naturally there are variations of the inventive aspects. It has been found that some other metal ions may be enzymatically reduced, including solutions of mercurous chloride, cesium chloride, lead nitrate, nickel sulfate, copper sulfate, palladium acetate and potassium ferrocyanide. Potassium ferrocyanide was reduced by peroxidase with hydroquinone adjusted to pH 10.

Other enzymes are also active toward reducing metal ions from their salts. For example, with a pretreatment of potassium tetrabromoaurate, catalase was found to reduce silver ions to silver metal when hydroquinone and hydrogen peroxide were included in a sodium citrate buffer at pH 3.8. Additionally lactoperoxidase was found to be active with silver ions.

While hydroquinone is presently the best known reducing agent, other reducing agents are also believed to be useful in practicing the invention, including, for example, n-propyl gallate, 4-methylaminophenol sulfate, 1,4 phenylenediamine, o-phenylenediamine, chloroquinone, bromoquinone, 2-methoxyhydroquinone, hydrazine, 1-phenyl-3-pyrazolidinone (phenidone aminophenol) and dithionite salts such as sodium dithionite. 1-phenyl-3-pyrazolidinone, sodium borohydride and boranes may work as a reducing agent without the need for $H_2O_2$.

Enzymes may be coupled one after another to produce the desired metal deposit. For example, glucose serves as a substrate for glucose oxidase, producing hydrogen peroxide. The hydrogen peroxide then serves as a substrate for peroxidase to deposit silver ions in the presence of hydroquinone, since hydrogen peroxide is used in that enzyme reaction.

The enzyme altered metal product may be soluble or dispersible in water. Naturally in other embodiments of the invention the altered metal products can be soluble in organic solvents. For example, aurothioglucose with hydroquinone and hydrogen peroxide, when exposed to horseradish peroxidase bound to nitrocellulose, turns an intense yellow at the location of the enzyme, if left undisturbed. However, rinsing or agitation easily disperses the color. This reaction may be coupled to an optical density reader or used in an ELISA format with a microtiter plate reader that will sense the newly formed colored product.

The inventive metal deposits, formed from particles or ions, may be further intensified using autometallography. As used herein "autometallography" is defined as a deposition of metal from metal ions in solution that specifically occurs on a nucleating metal surface. For example, it is known that if gold particles in the size range of about 1 to 50 nm are exposed to silver ions and a reducing agent, silver metal is deposited on the gold particles forming a composite particle. As more silver is deposited the composite particle increases in size. As the composite particles become larger, they become more visible and detectable.

Autometallography may be combined with the inventive enzymatic metal deposition. Once metal has been enzymatically deposited as a metal particle, the metal particle is subjected to an autometallographic solution. The autometallographic deposit forms a composite particle and amplifies the size of the enzymatically deposited metal particle so that the enzymatic metal deposits are more voluminous and hence easier to detect. The novel combination of enzymatic metal deposition in tandem with autometallography provides increased sensitivity and/or more rapid detection.

A further advantage of the use of enzymatic metal deposition in tandem with autometallography is that the autometallographic deposit may be a different metal from that of the enzymatically deposited particle. This permits overcoating of the original enzymatic metal deposit by one or more different autometallographically deposited metal layers. The autometallographic layer may also become the bulk of the composite particle if desired. It should be noted that the autometallographic coating, or coatings, may confer new properties to the enzymatic metal deposit, such as altered oxidation rates, magnetic properties, optical properties and electrical properties. For example, if gold is autometallographically deposited over an enzymatic silver deposit, this would confer improved chemical resistance as gold is more noble and more resistant to oxidation than the core silver deposit. Autometallographically depositing copper over a enzymatic metal deposit would confer the conductive, and other, properties of copper to the metal particle.

A wide variety of methods can be used to detect and observe the novel enzymatic metal deposits. In fact, the use of an enzymatic metal deposit overcomes many of the limitations of conventional enzyme-created fluorescent or colored particles. Some of the methods useful for detecting and observing an enzymatic metal deposit include:

Visual observation using the unaided eye. The enzymatic deposition of silver or silver after pretreating with gold typically results in a black or brown color due to the presence of finely divided metal. The color is easily seen by the unaided eye, especially against a light colored background.

Visual observation using a microscope. For higher resolution or more sensitive detection, the metal deposit may be viewed under a microscope. The metal is very dense and opaque, and may in many circumstances be easily detected by this density using bright field illumination.

Reflectance. Since metals reflect light, epi-illumination may be used either with or without a microscope. Additionally, metals repolarize light upon reflection, so crossed polarizers may be used to filter out reflections from non-metallic material, thus improving the signal-to-noise ratio.

Electron microscopy. Metals are clearly seen via electron microscopy due to their density in transmission electron microscopy. They also have high backscatter coefficients, and may be viewed with a backscatter detector on a scanning electron microscope. Metals also give off characteristic x-rays upon electron bombardment, so they may be detected by x-ray detectors, or electron energy loss spectrometers. Other methods include detection of the characteristic electron diffraction patterns of metals.

Polarographic, electrochemical, or electrical detection. Metals deposited on an electrode alter its properties. By probing with the proper currents and voltages, metal can be detected.

X-ray spectroscopy. Metals can be detected by x-ray induced fluorescence or x-ray absorption.

Chemical tests. Sensitive tests exist for chemically converting metals into products that are colored or otherwise detectable.

Mass detection. The mass of the deposited metal is detected using, for example, a quartz crystal mass balance. A quartz crystal in an inductance-resistance-capacitance (LRC) electronic circuit with an alternating voltage supply oscillates at some resonant frequency. If metal is deposited on the surface of the quartz crystal, this changes the mass of the crystal and its resonant frequency. This provides a very sensitive method for measuring mass changes.

Light scattering. Fine metal deposits will alter the light scattering of a solution or surface.

Other optical methods of detecting interaction of metals with light, including absorption, polarization and fluorescence.

Magnetic detection. The magnetic properties of the deposited metal can be detected using appropriate equipment such as magnets, coils, or sensing optical-magnetic property changes.

Autometallography. Further amplification of the signal may be achieved by applying additional metal ions and reducing agent and other additives to effect further metal deposition that specifically nucleates on the initial enzymatic metal deposit.

Scanning probe microscopy. Metal deposits may be recognized at high spatial resolution and sensitivity by the various scanning probe microscope techniques, including scanning tunneling microscopy (STM), atomic force microscopy (AFM), near field optical microscopy (NSOM) and other related techniques using piezoelectrically driven scanned tips.

Many of the enzymes useful in the present invention are purified from living cells. Bacteria and living organisms have functioning enzymes. Thus another aspect of the invention is enzymatic metal deposition, under appropriate conditions, in vivo. As one example, an initial developing mix comprising 1 mg/ml silver acetate, 2.5 mg/ml hydroquinone and 0.06% hydrogen peroxide in 0.1 M citrate buffer, pH 3.8 was prepared. When the initial developing mix was diluted 1 part developing mix: 1 part solution of a mixture of growing bacteria from pond water, the bacteria stained with silver metal deposits, but rapidly died.

As another example when the initial developing mix was diluted by adding 1 part of the above developing mix to 5 parts bacterial solution, the bacteria became black with internal silver deposits in a few minutes, but remained alive.

As a further example when the initial developing mix was diluted by adding 1 part of the above developing mix to 50 parts bacterial solution, the bacteria also became black with internal silver deposits, but over a longer period of about twenty four hours, and survived with no apparent toxicity. In each of the above examples the bacteria were intensely stained, much more so than with standard bacterial stains, and easily seen under a bright field light microscope. The use of enzymatic metal deposition in vivo provides a novel method of imaging and detecting bacteria and other live-cells.

The inventive enzymatic metal deposits are useful in a number of applications. Thus another aspect of the invention is the use of enzymatic metal deposits in such applications, including:

Immunohistochemistry and Immunocytochemistry:

Currently, antibodies are widely used to target antigens on cytologic specimens, tissue slices, and biopsies. The antibodies are then commonly detected by a variety of techniques including use of a secondary antibody that is biotinylated, followed by avidin-biotin-peroxidase complex (ABC complex), and development of a color with 3,3'-diaminobenzidine (DAB). Other detection methods include fluorescence and chemiluminescence. The present invention may be used as a detection scheme by supplying metal ions and a developing mix, preferably with a metal ion pretreatment, to the peroxidase localized to the antigen by the above described or analogous methods. Instead of depositing DAB, a metal, for example silver will be deposited. Enzymatic silver deposition has the advantage of better detectability not only by bright field microscopy (where a black deposit is formed), but also by reflectance microscopy, electron microscopy and other methods suited to metal detection. Sensitivity is therefore greatly improved over conventional methods.

Alternatively, the inventive metal clusters or colloids with surface enzyme substrates described above may be used to form antigen-specific deposits by enzymatic action. The enzymatic deposition of metals has a great advantage over simple targeting of metal nanoparticles attached to antibodies, as is commonly done using gold-antibody conjugates for electron microscopy, lateral flow tests, and other applications. One major advantage is that the metal or metal particles are continuously deposited by the enzyme, as long as more substrate is provided. In this way, huge amounts of metal product may be deposited compared to non-enzymatic targeting of metal particles, achieving a desirable amplification effect.

Thus, the popular DAB method used widely in pathology may be easily adapted to the more sensitive enzymatic metal deposition method described herein to easily achieve better results while requiring few changes and little additional expense.

In Situ Hybridization

Presently considerable laboratory and pathological testing is being done and it is desirable to have a sensitive method to detect DNA or RNA sequences. By hybridizing a complementary probe carrying a detectable moiety, these sequences can be found and quantified. However the limits of detection required to see single gene copies or low levels of expression exceed the capability of many methods. The present invention may be used to achieve sensitive detection by having the nucleic acid probe labeled with an enzyme, for example peroxidase, or to use multistep labeling, such as a biotinylated probe, followed by avidin-biotin-peroxidase complex. The peroxidase is then utilized as previously described to deposit metals. The enzymatically deposited metals are highly detectable and as further described below single gene sensitivity has been achieved using this novel method.

Lateral Flow, Blots, and Membrane Probing

A number of useful applications, such as lateral flow diagnostics (e.g., the "dipstick" pregnancy test kit), Western, Southern, and other blots, and other tests performed on membranes, are presently in use. Currently, these methods employ radioactive, fluorescent, colloidal gold, chemiluminescent, calorimetric, and other detection schemes, each having the previously discussed drawbacks and limitations. The inventive enzymatic metal deposition method is readily used with the above applications. For example, the target can be probed with a binding moiety that carries an enzyme, for example peroxidase. The binding moieties useful depend on the desired target and include, for example, antibody, antibody fragments, antigen, peptide, nucleic acids, nucleic acid probes, carbohydrates, drugs, steroids, natural products from plants and bacteria and synthetic molecules that have an affinity for binding particular targets. Enzymatic metal deposition is then applied, using either metal particles with substrate shells or metal ions and an appropriate developing mix, to deposit metal in the vicinity of the specific target site. The metal deposit may be in the form of an attached deposit or dispersed in solution. The enzymatically deposited metals are highly detectable and provide an extremely sensitive detection method.

Sensitive Detection of Antigens and Other Materials

Many other formats for detection of antigens and other materials have been devised, such as use of gels, microtiter plate systems and surface sensors. Most of these may easily be adapted to accommodate the present invention and substitute enzymatic deposition of metals and subsequent detection in place of conventional techniques. This would transform the conventional formats into new and improved formats having desirable characteristics such as higher sensitivity, lower cost, permanency of record and other advantages. Substitution of enzymatic deposition of metals and subsequent detection in place of conventional techniques also eliminates many of the disadvantages of conventional systems, such as use of radioactive materials, bleaching, transitory products and high expense.

Electron Microscope Probes

Small amounts of metals are easily detected in electron microscopes by their density, backscatter, x-ray emission or energy loss. The invention herein can be used to specifically target antigens or other sites, initially with an enzyme followed by deposition of metal. The enzymatically deposited detectable metal allows the targeted sites to be analyzed with high specificity and sensitivity.

Nanotechnology and Nanofabrication

Since the present invention provides for deposition of metals at enzyme locations, unique materials and objects may be created. For example, a structure such as the regular arrays of muscle tissue may be treated with antibodies to the Z band. Then a secondary antibody conjugated to peroxidase is added to the muscle tissue. Finally, the enzyme is given a silver or gold pretreatment, followed by the enzymatic metal deposition. The Z bands are then converted to metal deposits creating a nanostructure of finely spaced metallic bands that would be difficult to fabricate by other means. The creation of many other objects and patterned objects ultimately containing metal using the present invention can be imagined by those skilled in the art and all such embodiments are encompassed by this invention. It should be noted that enzymatic deposition of magnetic metals will be useful in computer technology and data storage.

Biosensors

The present invention can be applied to provide a range of novel biosensors. Several modes of construction are possible, including amperometric, potentiometric, and optical. For example, an analyte will undergo an enzyme reaction as a substrate. The enzyme reaction may produce directly, or be coupled to another enzyme reaction to produce, a reducing agent or hydrogen peroxide. As a more specific example glucose oxidase oxidizes glucose to gluconic acid and hydrogen peroxide. Thus the enzyme reaction provides the hydrogen peroxide required for the reduction of a metal by peroxidase. The reduced metal is deposited on an electrode, altering the electrode current. The deposited metal can also be sensed polarographically by an alternating current. Potentiometric detection can be used by sensing the change in metal ion concentrations resulting from enzyme deposition. Optical biosensors can be made based on the large light absorption and scattering changes provided by enzymatic metal deposition.

Remediation

Mercury, lead and other toxic metals may be altered by the novel enzyme action described herein to convert toxic metal ions into insoluble metal, thus fixing the toxic substances and preventing the toxic ions from leeching into groundwater tables. The novel enzymatic action is useful to remove toxic metals from any water stream, such as manufacturing or water treatment plants.

Bacteria and Live Cell Staining

The instant invention has been used to intensely stain live bacteria, to a much higher degree than achievable using conventional bacterial stains. This has important implications for detection of bacteria in water, foods, and samples from patients. Simple metal detectors based on, for example, light scattering are made possible by the inventive enzyme metal deposit. Because the enzymatic metal deposit can be detected with high sensitivity, little or no culturing need be done. The elimination of the hours or days needed to grow pathogens to a detectable level so that they may be screened for antibiotic sensitivity solves a problem inherent with current technology. Naturally other live cells and organisms may similarly be stained with novel metal depositions using enzymes endogenous to that cell or organism.

The present invention also provides a test kit for enzymatically depositing metal in a zero oxidation state. The test kit comprises means for enzymatically depositing metal in a zero oxidation state, and the enzymatically deposited metal provides a detectable test result.

Having generally described certain aspects of the invention, the following examples are included for purposes of illustration so that the invention may be more readily understood and are in no way intended to limit the scope of the invention unless otherwise specifically indicated.

EXAMPLES

Example 1

Enzymatic Deposition of Silver Metal

One microgram of horseradish peroxidase was applied to a nitrocellulose membrane and allowed to dry. The membrane was then optionally blocked using 4% bovine serum albumin and washed. A solution containing 2.5 mg/ml hydroquinone and 1 mg/ml silver acetate in a 0.1 M citrate buffer, pH 3.8 was applied. Next, hydrogen peroxide was added and mixed to a final concentration of 0.03 to 0.06%. Silver deposition selectively occurred at the peroxidase spot as evidenced by a black product. No deposit occurred if the hydrogen peroxide was omitted.

Example 2

Enhanced Enzymatic Deposition of Silver Metal; Pretreatment with Silver Ions

One microgram of horseradish peroxidase was applied to a nitrocellulose membrane and allowed to dry. The membrane was then optionally blocked using 4% bovine serum albumin and washed. A solution of 2 mg/ml silver acetate in water was applied for three to five minutes, then washed with water. A solution containing 2.5 mg/ml hydroquinone and 1 mg/ml silver acetate in a 0.1 M citrate buffer, pH 3.8 was applied. Next, hydrogen peroxide was added and mixed to a final concentration of 0.03 to 0.06%. Silver deposition immediately and selectively occurred at the peroxidase spot as evidenced by an intense black product. No silver deposit occurred if the hydrogen peroxide was omitted.

Example 3

Enhanced Enzymatic Deposition of Silver Metal; Pretreatment with Gold Ions

One microgram of horseradish peroxidase was applied to a nitrocellulose membrane and allowed to dry. The membrane was then optionally blocked using 4% bovine serum albumin and washed. A solution of 0.1 mg/ml potassium tetrabromoaurate in water was applied for five minutes, then briefly washed with water. A solution containing 2.5 mg/ml hydroquinone and 1 mg/ml silver acetate in a 0.1 M citrate buffer, pH 3.8 was applied. Next, hydrogen peroxide was added and mixed to a final concentration of 0.03 to 0.06%. Silver deposition immediately and selectively occurred at the peroxidase spot as evidenced by an intense brown-black product.

Example 4

Enzymatic Deposition of Gold Nanoparticles

Gold nanoparticles having a diameter in the range of about 1–3 nm and a nominal diameter of 1.4 nm were prepared and ligand stabilized with 4-hydroxythiophenol and a glutathione such that the 4-hydroxythiophenol was 30% of the ligand mixture. The gold particles were purified on an Amicon GH25 gel filtration column to remove unreacted materials. One microgram of horseradish peroxidase was applied to a nitrocellulose membrane and allowed to dry. The membrane was then optionally blocked using 4% bovine serum albumin and washed. A $10^{-6}$ M solution of the functionalized gold nanoparticles in 50 mM Tris buffer, pH 7.6 was applied. Next, hydrogen peroxide was added and mixed to a final concentration of 0.03 to 0.06%. A brown spot appeared at the peroxidase.

Example 5

Sensitive Immunological Detection of Antigen Using Enzymatic Metal Deposition

Figure 3:
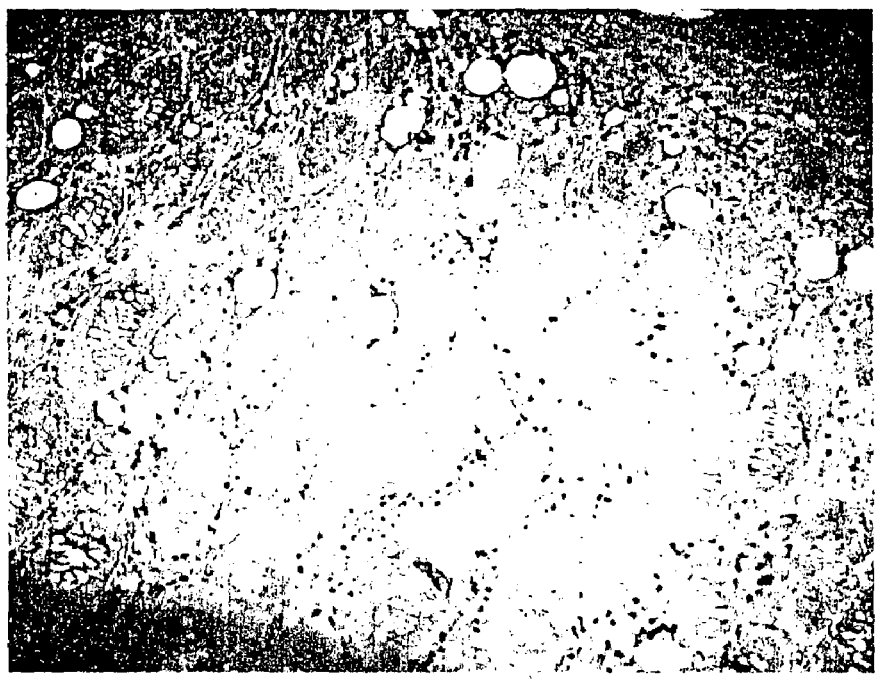
FIG. 3 illustrates the results of a conventional immunostaining test using an antibody, peroxidase, and the substrate AEC (3-amino-9-ethylcarbazole). Human colon carcinoma tissue was fixed in formalin and embedded in paraffin. Next it was sectioned and placed on glass slides for the light microscopy. Sections were deparaffinized with toluene, and rehydrated through successive washes in 100%, 95%, 80%, 70% ethanol, and finally phosphate buffered saline (PBS: 0.01M sodium phosphate, 0.14M sodium chloride, pH 7.4). Endogenous peroxide was quenched by incubating with 2 drops of 3% hydrogen peroxide for 5 minutes, followed by washing in PBS. Sections were then incubated with a biotinylated monoclonal antibody to an antigen in the section for 1 hour at room temperature. After washing with PBS, the sections were next incubated with a streptavidin-peroxidase conjugate for 20 min. After washing with PBS, the substrate AEC was applied in 50 mM acetate buffer, pH 5.0 containing 0.03% hydrogen peroxide. A reddish color developed over certain areas targeted by the monoclonal antibody. The slide was washed with water to stop the reaction after 20 min. Full width of bright field light micrograph shown is 250 microns.
Figure 4:
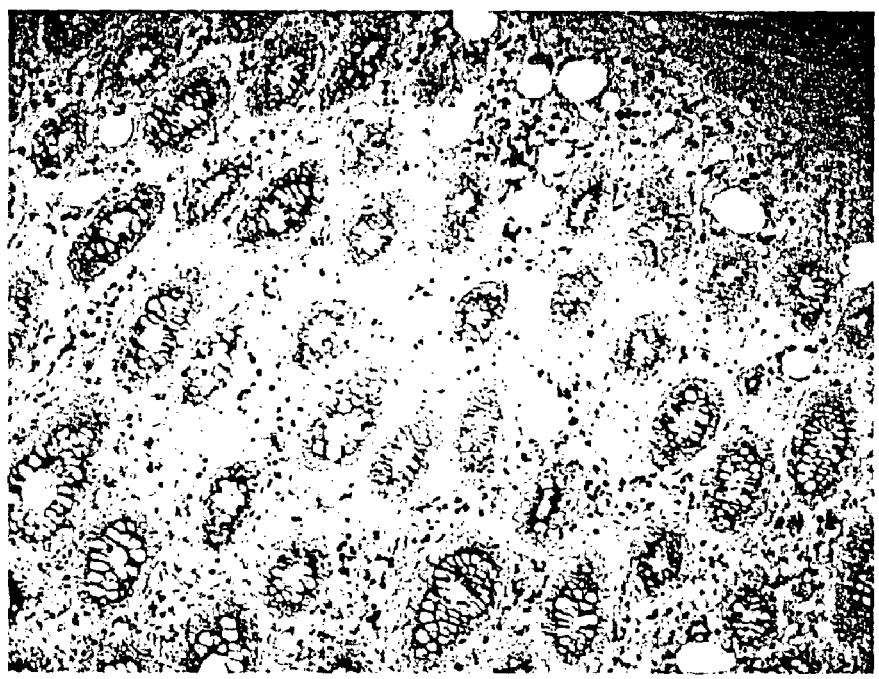
FIG. 4. illustrates the results of an immunostaining test incorporating an aspect of the invention using an antibody, peroxidase, and enzyme metal deposition. Similarly to the procedure used in FIG. 3, human colon carcinoma tissue was fixed in formalin and embedded in paraffin. Next it was sectioned and placed on glass slides for the light microscopy. Sections were deparaffinized with toluene, and rehydrated through successive washes in 100%, 95%, 80%, 70% ethanol, and finally phosphate buffered saline (PBS: 0.01M sodium phosphate, 0.14M sodium chloride, pH 7.4). Endogenous peroxide was quenched by incubating with 2 drops of 3% hydrogen peroxide for 5 minutes, followed by washing in PBS. Sections were then incubated with a biotinylated monoclonal antibody to an antigen in the section for 1 hour at room temperature. After washing with PBS, the sections were next incubated with a streptavidin-peroxidase conjugate for 20 min. After washing with water, the sections were incubated with a solution of 2 mg/ml silver acetate in water for three minutes, then washed with water. A solution containing 2.5 mg/ml hydroquinone and 1 mg/ml silver acetate in a 0.1 M citrate buffer, pH 3.8 was applied, and 3% hydrogen peroxide was added and mixed to achieve a final hydrogen peroxide concentration of 0.06%. Slides were observed in the light microscope and metal deposition was stopped with a water wash after 15 min. Intense silver metal staining was observed at the expected locations. Compared to the conventional immunostaining using the AEC substrate shown in FIG. 3, the enzyme metal deposition shown here had a similar distribution to the AEC red product, but the metal deposition was more intense, of better resolution, and clearly more sensitive. Controls where the streptavidin-peroxidase was deleted from the procedure showed little background and were clearly negative. Full width of bright field light micrograph shown is 250 microns.

Human colon carcinoma resected material was fixed in formalin, paraffin embedded, sectioned, and placed on glass slides for light microscopy. Sections were deparaffinized with toluene, and rehydrated through successive washes in 100%, 95%, 80%, 70% ethanol, and finally phosphate buffered saline (PBS: 0.01M sodium phosphate, 0.14M sodium chloride, pH 7.4). Endogenous peroxide was quenched by incubating with 2 drops of 3% hydrogen peroxide for 5 minutes, followed by washing in PBS. Sections were then incubated with a biotinylated monoclonal antibody to an antigen in the section for 1 hour at room temperature. After washing with PBS, the sections were next incubated with a streptavidin-peroxidase conjugate for 20 min. After washing with water, the sections were incubated with a solution of 2 mg/ml silver acetate in water for three minutes, then washed with water. A solution containing 2.5 mg/ml hydroquinone and 1 mg/ml silver acetate in a 0.1 M citrate buffer, pH 3.8 was applied, and hydrogen peroxide was added and mixed to a final concentration of 0.06%. Slides were observed in the light microscope and metal deposition was stopped with a water wash after 15 min. As shown in FIG. 4, intense silver metal staining was observed at the antigenic positions detected using conventional means. Parallel slides done using aminoethyl carbinol as the peroxidase substrate showed a similar distribution of red product staining, but it was much less intense, of poorer resolution and clearly less sensitive than the metal deposition slides. See FIG. 3. Controls where the streptavidin-peroxidase was deleted from the procedure showed little background and were clearly negative.

Example 6

Detection of a Single Gene in a Single Cell Using Enzymatic Metal Deposition

Figure 5:
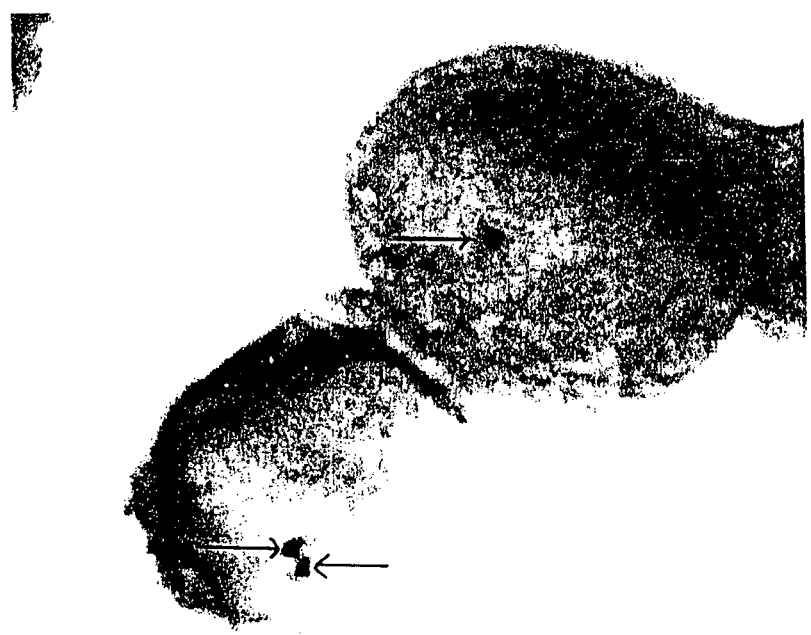
FIG. 5. illustrates the detection of a single gene in a single cell using the inventive enzyme metal deposition. Silver deposits appear at the targeted gene site and are evident in the bright field light micrograph. This demonstrates the high sensitivity of enzyme metal deposition to detect single gene copies within individual cells. In the micrograph, the lower cell shows two dense black spots, indicated with arrows, close together, representing the gene on the pair of chromosomes, as expected, since cells have pairs of chromosomes. In the upper cell, two dense spots, indicated with arrows, are also seen in the cell; they are more widely separated since these cells are in interphase, and the chromosomes are randomly placed. Full width of bright field light micrograph is 20 microns.

With reference to FIG. 5, human breast cancer biopsies were fixed, embedded and sectioned. In situ hybridization was performed by standard procedures, such as removal of paraffin, treatment with proteinase K, and hybridization with a fluoresceinated probe for the Her-2/neu gene. After hybridization, and washing, a biotinylated anti-fluorescein antibody was applied, followed by streptavidin conjugated to horseradish peroxidase. Then the sample was pretreated with a gold salt solution, and after washing was exposed to silver acetate, hydroquinone and hydrogen peroxide. Silver deposits appeared at the targeted gene site and were evident by bright field light microscopy. This demonstrated the high sensitivity of the enzyme metal deposition to detect single gene copies within individual cells.

More specifically, the formalin fixed, paraffin embedded and sectioned tissue was deparaffinized by treating with xylene 2×5 min. This was followed by 100% alcohol (2×1 min), 95% alcohol (2×1 min), a water soak (5 min), Dako-Target retrieval solution (40 min at 95° C., then 20 min cool down at room temperature (RT)), a water rinse (5 min with several changes), proteinase K (Dako 1:5000 in 50 mM Tris 5 min @ RT), a water rinse (1×1 min), 80% alcohol (1×1 min), 95% alcohol (1×1 min), 100% alcohol (1×1 min, allowing to air dry), probe addition (10 microliters of probe, coverslip added and sealed; stored overnight), codenaturation (6 min @ 90° C.), hybridization (37° C. overnight), coverslip soak (remove cement, 2×SSC buffer soak for 5 min), stringent wash (0.5×SSC, 72C, 5 min), wash in dd (double distilled) water (2 min), Lugol's iodine (immerse slide for 5 min), dd water (3 rinses), 2.5% sodium thiosulfate (immerse slide for a few sec until tissue clears), dd water (3–5 rinses, 7 min total), 1× PBS (phosphate buffered saline)+0.1% Tween 20 (3 min RT), primary antibody incubation (Anti-fluorescein-biotin, 1:100 in PBS, pH 7.6 with 1% BSA (bovine serum albumin), 50 microliters, apply plastic coverslip, 30 min @ RT), 1×PBS+0.1% Tween 20 (3×5 min, RT), PBS, ph7.6, 0.1% fish gelatin (immerse for 5 min), streptavidin-peroxidase (1:200, diluted with PBS pH 7.6 with 1% BSA, 50 microliters, plastic coverslip, 60 min @ RT), wash PBS pH 7.6 (2×5 min), PBS pH 7.6, 0.1% fish gelatin (immerse for 5 min), rinse in dd water (10 min several changes), 0.1 mg/ml potassium tetrabromoaurate in water (5 min), dd water (3×1 min), substrate silver ions and developing mix (2.5 mg/ml hydroquinone, 1 mg/ml silver acetate, 0.06% hydrogen peroxide in 0.1 M citrate buffer, pH 3.8; observe development), stop metal deposition with water wash (2×3 min), hematoxylin stain (1 min), water rinse, alcohol-xylene.

Example 7

Enzymatic Deposition of Gold Particles Having 3,3'-Diaminobenzidine Attached Gold nanoparticles having a diameter in the range of about 1–3 nm were synthesized by reduction of potassium tetrabromaurate with sodium borohydride, including the thiol ligand glutathione and 3,3'-diaminobenzidine. The nanoparticles were then purified from starting materials by size exclusion column chromatography on an Amicon GH25 column with water as the eluent. Particles were then incubated with horseradish peroxidase immobilized on a nitrocellulose membrane, with addition of hydrogen peroxide to a final concentration of 0.03%. Gold particles were found to deposit selectively at the peroxidase location.

Example 8

Detection of Live Bacteria Using Enzymatic Metal Deposition

Figure 6:
FIG. 6. illustrates detection of live bacteria using the inventive enzyme metal deposition. A sample of water microscopically revealed bacterial organisms under phase contrast light microscopy. 1000 parts of the water sample was incubated with 1 part of the developing mix (comprising 1 mg/ml silver acetate, 2.5 mg/ml hydroquinone and 0.06% hydrogen peroxide in 0.1 M citrate buffer, pH 3.8). The live bacteria became intensely stained black with silver deposits and were easily seen in bright field. The bacteria were actively moving, so were captured with a shutter speed of 0.08 sec under bright field conditions using an oil immersion lens at a magnification of 1000×. Most of the bacteria (black spots) were round, or cocci bacteria, but a few rodlike (bacilli) bacteria can be seen in the micrograph. All of the bacteria remained alive for more than a month. Full width of this micrograph is 100 microns.

A sample of pond water microscopically revealed bacterial organisms under phase contrast light microscopy. An aliquot was mixed, 1 part developing mix to 5 parts pond water. The developing mix consisted of 1 mg/ml silver acetate, 2.5 mg/ml hydroquinone and 0.06% hydrogen peroxide in 0.1 M citrate buffer, pH 3.8. Over time the bacteria became dark, and after a few minutes the bacteria were visible by bright field microscopy (whereas they were not seen in this mode previously). The bacteria remained alive. In another case, 1000 parts tap water was incubated with 1 part of the developing mix. After several days, live bacteria were intensely stained black with silver deposits and were easily seen in bright field. See FIG. 6. The bacteria remained alive for more than a month.

Example 9

Enzymatic Deposition of Iron

One microgram of horseradish peroxidase was adsorbed to nitrocellulose, dried, then blocked with 4% bovine serum albumin. A solution containing 1% potassium ferrocyanide, 0.5% hydroquinone, and 0.06% hydrogen peroxide in a 0.1 M citrate buffer, pH 3.8 was incubated with the target enzyme. In a few minutes, a deposit of iron was visible as a dense spot at the peroxidase site.

Example 10

Enzymatic Deposition of Mercury

One microgram of horseradish peroxidase was adsorbed to nitrocellulose, dried, then blocked with 4% bovine serum albumin. A solution containing 0.5% mercurous chloride, 0.25% hydroquinone, and 0.06% hydrogen peroxide in a 0.1 M citrate buffer, pH 3.8 was incubated with the target enzyme. In a few minutes, a deposit of mercury was visible as a dense spot at the peroxidase site.

Example 11

Enzymatic Deposition of Nickel

One microgram of horseradish peroxidase was adsorbed to nitrocellulose, dried, then blocked with 4% bovine serum albumin. A solution containing 5% nickel sulfate, 0.25% hydroquinone, and 0.06% hydrogen peroxide in a 0.1 M citrate buffer, pH 3.8 was incubated with the target enzyme. In a few minutes, a deposit of nickel was visible as a dense spot at the peroxidase site.

Example 12

Enzymatic Deposition of Copper

One microgram of horseradish peroxidase was adsorbed to nitrocellulose, dried, then blocked with 4% bovine serum albumin. A solution containing 5% copper sulfate, 0.25% hydroquinone, and 0.06% hydrogen peroxide in a 0.1 M citrate buffer, pH 3.8 was incubated with the target enzyme. In a few minutes, a deposit of copper was visible as a dense spot evident at the peroxidase site.

Example 13

Lactoperoxidase Catalyzed Deposition of Silver

Several beads of immobilized lactoperoxidase were mixed with a solution containing 0.25% hydroquinone, 0.1% silver acetate, and 0.06% hydrogen peroxide in a 0.1 M citrate buffer, pH 3.8. Many of the beads turned black in color as a result of silver deposition.

Example 14

Enzymatic Deposition of Silver Using Catalase

One microgram of catalase was adsorbed to nitrocellulose, dried, then blocked with 4% bovine serum albumin. An aqueous solution containing 0.01% potassium tetrabromoaurate was preincubated with the enzyme, then washed. Next, a solution of 0.25% hydroquinone, 0.1% silver acetate, and 0.06% hydrogen peroxide in a 0.1 M citrate buffer, pH 3.8 was incubated with the target enzyme. In a few minutes, a deposit of silver was visible as a dense spot at the catalase site.

Example 15

Soluble Colored Compound Containing Gold Formed Upon Enzyme Action on Aurothioglucose One microgram of horseradish peroxidase was adsorbed to nitrocellulose, dried, then blocked with 4% bovine serum albumin. A solution containing 0.5% aurothioglucose was incubated with the enzyme in a solution also containing 0.25% hydroquinone and 0.06% hydrogen peroxide in a 0.1 M citrate buffer, pH 3.8. In a few minutes, an intense yellow colored gold product was evident at the peroxidase site. The gold product was soluble and could be easily redistributed in the solution if mixed.

Example 16

Enzymatic Deposition of Gold Particles Stabilized with Thioglucose

Gold nanoparticles having thioglucose bound to their surfaces were prepared. The particles were purified by gel filtration chromatography to remove any excess reactants. One microgram of horseradish peroxidase was adsorbed to nitrocellulose, dried, then blocked with 4% bovine serum albumin. A solution containing 0.5 O.D. at 420 nm of the gold particles was incubated with the enzyme in a solution also containing 0.25% hydroquinone and 0.06% hydrogen peroxide in a 0.1 M citrate buffer, pH 3.8. In a few minutes, an brown product was evident at the peroxidase site, indicating deposition of the nanoparticles.

Example 17

Sensitive Immunological Detection Using Enzymatic Metal Deposition

Human breast biopsy material was prepared in a manner similar to Example 5. Four tests were done on the biopsy material using the inventive enzymatic metal deposition and conventional (DAB) staining techniques:

1. breast cancer, testing for and localizing the estrogen receptor (ER);

2. breast cancer, testing for and localizing the progesterone receptor (PR);

3. breast cancer, testing for and localizing the Her 2-neu oncoprotein; and 4. breast cancer, testing for and localizing the Her 2-neu oncoprotein.

Slides were observed in the light microscope and metal deposition was stopped with a water wash after 15 min. The samples prepared using the inventive enzymatic metal deposition method had deposits of much higher resolution than the conventionally stained test samples, so that, for example, membrane proteins were clearly localized to the membrane. The metal deposit signal was very intense and black with a higher density than the conventionally stained test samples. There was no background using the inventive method. Parallel slides done using DAB resulted in a brown signal that was less dense than the signal produced using the inventive method.

Example 18

Enzymatic Deposition of Metal Using 4-Methylaminophenol Sulfate as the Reducing Agent One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 5 microliters of a 5 mg/ml solution of 4-methylaminophenol sulfate (also called metol or elon) was applied with mixing. An identical test was prepared except that additionally 3 microliters of a 3% hydrogen peroxide solution was added with mixing. Only the sample with the hydrogen peroxide showed specific deposition of silver metal at the horseradish peroxidase site on the nitrocellulose, as evidenced by a dark metallic spot congruent with the position of the bound enzyme.

Example 19

Enzymatic Deposition of Metal Using 1,4 Phenylenediamine as the Reducing Agent One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 5 microliters of a 5 mg/ml solution of 1,4 phenylenediamine was applied with mixing. An identical test was prepared except that additionally 3 microliters of a 3% hydrogen peroxide solution was added with mixing. Only the sample with the hydrogen peroxide showed specific deposition of silver metal at the horseradish peroxide site on the nitrocellulose, as evidenced by a dark metallic spot congruent with the position of the bound enzyme.

Example 20

Enzymatic Deposition of Metal Using O-Phenylenediamine as the Reducing Agent One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 5 microliters of a 5 mg/ml solution of o-phenylenediamine was applied with mixing. An identical test was prepared except that additionally 3 microliters of a 3% hydrogen peroxide solution was added with mixing. Only the sample with the hydrogen peroxide showed specific deposition of silver metal at the horseradish peroxide site on the nitrocellulose, as evidenced by a dark metallic spot congruent with the position of the bound enzyme.

Example 21

Enzymatic Deposition of Metal Using Chloroquinone as the Reducing Agent

One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 5 microliters of a 5 mg/ml solution of chloroquinone was applied with mixing. An identical test was prepared except that additionally 3 microliters of a 3% hydrogen peroxide solution was added with mixing. Only the sample with the hydrogen peroxide showed specific deposition of silver metal at the horseradish peroxide site on the nitrocellulose, as evidenced by a dark metallic spot congruent with the position of the bound enzyme.

Example 22

Enzymatic Deposition of Metal Using Bromoquinone as the Reducing Agent

One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 5 microliters of a 5 mg/ml solution of bromoquinone was applied with mixing. An identical test was prepared except that additionally 3 microliters of a 3% hydrogen peroxide solution was added with mixing. Only the sample with the hydrogen peroxide showed specific deposition of silver metal at the horseradish peroxide site on the nitrocellulose, as evidenced by a dark metallic spot congruent with the position of the bound enzyme.

Example 23

Enzymatic Deposition of Metal Using 2-Methoxyhydroquinone as the Reducing Agent

One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 5 microliters of a 5 mg/ml solution of 2-methoxyhydroquinone was applied with mixing. An identical test was prepared except that additionally 3 microliters of a 3% hydrogen peroxide solution was added with mixing. Only the sample with the hydrogen peroxide showed specific deposition of silver metal at the horseradish peroxide site on the nitrocellulose, as evidenced by a dark metallic spot congruent with the position of the bound enzyme.

Example 24

Enzymatic Deposition of Metal Using Hydrazine as the Reducing Agent

One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 5 microliters of hydrazine was applied with mixing. An identical test was prepared except that additionally 3 microliters of a 3% hydrogen peroxide solution was added with mixing. Only the sample with the hydrogen peroxide showed specific deposition of silver metal at the horseradish peroxide site on the nitrocellulose, as evidenced by a dark metallic spot congruent with the position of the bound enzyme.

Example 25

Enzymatic Deposition of Metal Using Dithionite Salt (e.g., Sodium Dithionite) as the Reducing Agent One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 5 microliters of a 5 mg/ml solution of sodium dithionite was applied with mixing. An identical test was prepared except that additionally 3 microliters of a 3% hydrogen peroxide solution was added with mixing. Only the sample with the hydrogen peroxide showed specific deposition of silver metal at the horseradish peroxide site on the nitrocellulose, as evidenced by a dark metallic spot congruent with the position of the bound enzyme.

Example 26

Enzymatic Deposition of Metal Using Thioglucose as the Reducing Agent

One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 5 microliters of a 100 mg/ml solution of thioglucose was applied with mixing. An identical test was prepared except that additionally 3 microliters of a 3% hydrogen peroxide solution was added with mixing. Only the sample with the hydrogen peroxide showed specific deposition of silver metal at the horseradish peroxide site on the nitrocellulose, as evidenced by a dark metallic spot congruent with the position of the bound enzyme.

Example 27

Enzymatic Deposition of Metal Using Glucosamine as the Reducing Agent

One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 20 microliters of a 5 mg/ml solution of glucosamine was applied with mixing. An identical test was prepared except that additionally 3 microliters of a 3% hydrogen peroxide solution was added with mixing. Only the sample with the hydrogen peroxide showed specific deposition of silver metal at the horseradish peroxide site on the nitrocellulose, as evidenced by a dark metallic spot congruent with the position of the bound enzyme.

Example 28

Enzymatic Deposition of Metal Using Sodium Metabisulfite as the Reducing Agent

One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 5 microliters of a 5 mg/ml solution of sodium metabisulfite was applied with mixing. An identical test was prepared except that additionally 3 microliters of a 3% hydrogen peroxide solution was added with mixing. Only the sample with the hydrogen peroxide showed specific deposition of silver metal at the horseradish peroxide site on the nitrocellulose, as evidenced by a dark metallic spot congruent with the position of the bound enzyme.

Example 29

Enzymatic Deposition of Metal Using Aminophenol as the Reducing Agent

One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 5 microliters of a 5 mg/ml solution of aminophenol was applied with mixing. An identical test was prepared except that additionally 3 microliters of a 3% hydrogen peroxide solution was added with mixing. The sample with the hydrogen peroxide showed specific deposition of silver metal at the horseradish peroxide site on the nitrocellulose, as evidenced by a dark metallic spot congruent with the position of the bound enzyme. A spot over the enzyme also developed in the sample without hydrogen peroxide, indicating that the hydrogen peroxide may not be required in this case.

Example 30

Enzymatic Deposition of Metal Using 1-Phenyl-3-Pyrazolidinone (Phenidone) as the Reducing Agent One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 3.4. Next, 5 microliters of a 5 mg/ml solution of 1-phenyl-3-pyrazolidinone I was applied with mixing. An identical test was prepared except that additionally 3 microliters of a 3% hydrogen peroxide solution was added with mixing. The sample with the hydrogen peroxide showed specific deposition of silver metal at the horseradish peroxide site on the nitrocellulose, as evidenced by a dark metallic spot congruent with the position of the bound enzyme. A spot over the enzyme also developed in the sample without hydrogen peroxide, indicating that the hydrogen peroxide may not be required in this case.

Example 31

Enzymatic Deposition of Metal Using Borohydride as the Reducing Agent

One microliter of a 0.1 mg/ml solution of horseradish peroxidase was applied to nitrocellulose paper and allowed to dry. 50 microliters of a 2 mg/ml solution of silver acetate was applied, followed by addition of 50 microliters of 0.1 M sodium citrate buffer, pH 8. Next, 5 microliters of a 1 mg/ml solution of sodium borohydride was applied with mixing. An identical test was prepared except that additionally 3 microliters of a 3% hydrogen peroxide solution was added with mixing. The sample with the hydrogen peroxide showed specific deposition of silver metal at the horseradish peroxide site on the nitrocellulose, as evidenced by a dark metallic spot congruent with the position of the bound enzyme. A spot over the enzyme also developed in the sample without hydrogen peroxide, indicating that the hydrogen peroxide may not be required in this case.

Those skilled in the art will recognize, or be able to ascertain with no more than routine experimentation, many equivalents to the specific embodiments of the invention disclosed herein. Such equivalents are intended to be encompassed by the scope of the invention.

What is claimed is:

1. A kit for detecting Her-2/neu gene or protein in a test sample, comprising:
    metal ions selected from the group consisting of silver, gold, iron, mercury, nickel, copper, platinum, palladium, cobalt, iridium ions and a mixture thereof; an oxidizing agent; a reducing agent; an enzyme; and a binding moiety that binds to Her-2/neu gene or protein in the test sample.

2. The kit of claim 1, wherein the binding moiety is a nucleic acid probe predetermined to bind to Her-2/neu gene.

3. The kit of claim 2, wherein the nucleic acid probe is labeled with biotin.

4. The kit of claim 1, wherein the binding moiety is a primary antibody predetermined to bind to Her-2/neu protein.

5. The kit of claim 4, wherein the enzyme is conjugated to a secondary antibody that binds to the primary antibody.

6. The kit of claim 1, wherein the enzyme is peroxidase; the metal ions are silver ion; the oxidizing agent is hydrogen peroxide; and the reducing agent is hydroquinone.

* * * * *